United States Patent [19]

Kruse et al.

[11] Patent Number: 4,874,557
[45] Date of Patent: Oct. 17, 1989

[54] PROCESS FOR THE PREPARATION OF PERFLUORINATED CARBONYL FLUORIDES

[75] Inventors: Alfred Kruse, Kelkheim; Günter Siegemund, Hofheim am Taunus; Werner Schwertfeger, Langgöns, all of Fed. Rep. of Germany

[73] Assignee: Hoechst Aktiengesellschaft, Frankfurt am Main, Fed. Rep. of Germany

[21] Appl. No.: 266,919

[22] Filed: Nov. 3, 1988

[30] Foreign Application Priority Data

Nov. 7, 1987 [DE] Fed. Rep. of Germany ....... 3737920

[51] Int. Cl.$^4$ ............................................. C07C 51/29
[52] U.S. Cl. ................................................. 562/851
[58] Field of Search ................................... 260/544 F

[56] References Cited

U.S. PATENT DOCUMENTS

| | | | |
|---|---|---|---|
| 3,412,148 | 11/1968 | Arbogast | 260/544 F |
| 3,847,978 | 11/1974 | Sianesi et al. | 260/544 F |
| 3,896,167 | 7/1975 | Sianesi et al. | 260/544 F |
| 3,896,179 | 7/1975 | Resnick | 260/544 F |
| 4,035,388 | 7/1977 | Martini et al. | 260/544 F |
| 4,057,584 | 11/1977 | Touzuka et al. | 260/544 F |
| 4,118,421 | 10/1978 | Martini et al. | 260/544 F |
| 4,151,200 | 4/1979 | Yamabe et al. | 260/544 F |
| 4,303,593 | 12/1981 | Kühne | 260/544 F |
| 4,345,092 | 8/1982 | Resnick | 260/544 F |
| 4,474,700 | 10/1984 | Krespan | 260/544 F |
| 4,526,948 | 7/1985 | Resnick | 260/544 F |
| 4,556,747 | 12/1985 | Resnick | 260/544 F |
| 4,590,015 | 5/1986 | Resnick | 260/544 F |
| 4,749,526 | 6/1988 | Flynn | 260/544 F |

FOREIGN PATENT DOCUMENTS

| | | |
|---|---|---|
| 0070635 | 1/1983 | European Pat. Off. . |
| 0150618 | 8/1985 | European Pat. Off. . |
| 2627986 | 1/1978 | Fed. Rep. of Germany . |
| 3130859 | 4/1982 | Fed. Rep. of Germany . |

OTHER PUBLICATIONS

Hans Millauer et al., Angew. Chem. Int'l. Ed., (English), 24, 161-179, (1985).

*Primary Examiner*—Paul J. Killos

[57] ABSTRACT

The invention relates to a process for the preparation of perfluorinated carbonyl fluorides of the formula

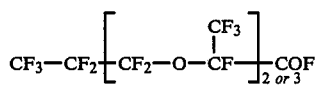

(I)

by oligomerization of hexafluoropropene oxide in the presence of a catalyst. The catalyst comprises a mixture of an alkali metal fluoride, a carboxylic acid dinitrile and a polyethylene glycol dimethyl ether.

8 Claims, No Drawings

PROCESS FOR THE PREPARATION OF PERFLUORINATED CARBONYL FLUORIDES

Process for the preparation of perfluorinated carbonyl fluorides

The invention relates to a process for the preparation of perfluorinated carbonyl fluorides of the formula

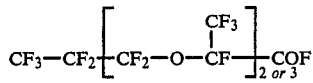
(I)

by oligomerisation of hexafluoropropene oxide in the presence of a catalyst. The two compounds mentioned are therefore the trimer and the tetramer of hexafluoropropene oxide. They are useful intermediates in the field of organic fluorine chemistry. In particular, they are employed for the preparation of perfluoropolyethers which are employed, for example, as inert liquids, or for the preparation of perfluorinated vinyl ethers which are used as comonomers for the preparation of fluorinated plastics.

The oligomerisation of hexafluoropropene oxide (HFPO) in the presence of various catalysts is already known and proceeds according to the following equation:

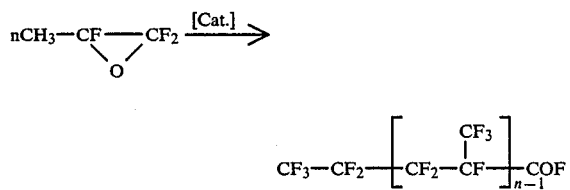

A comprehensive review of this reaction including the catalysts used was given in Angew. Chem. Int. Ed. Engl. 24, 161–178 (1985) (in particular p. 165, 166). The possibilities of use mentioned for the trimer and the tetramer are referred to therein on p. 176–177.

The selective dimerisation of HFPO is already known (U.S. Pat. No. 4,081,467, U.S. Pat. No. 3,896,179). However, mixtures having a high molecular weight and/or a wide product spectrum in general result in further oligomerisation of HFPO.

According to German Offenlegungsschrift No. 2,627,986, the trimer and the tetramer of the formula (I) can be obtained by polymerisation of HFPO by the catalytic action of bisdialkylaminodifluoromethanes. The disadvantage of this process is that very long reaction times, low temperatures from $-20°$ C. to $-30°$ C., complicated preparation of catalyst and the use of hexafluoropropene/HFPO mixtures are necessary.

The object, then, was to find a highly efficient catalyst system with as selective an action as possible for a commercially utilisable oligomerisation of HFPO to the trimer and also to the tetramer.

The invention relates to a process for the preparation of perfluorinated carbonyl fluorides of the formula

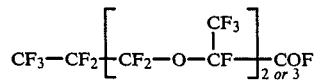
(I)

by oligomerisation of hexafluoropropene oxide in the presence of a catalyst, wherein the catalyst comprises an alkali metal fluoride, a carboxylic acid dinitrile and an ether of the formula $$CH_3-O-(CH_2CH_2-O)_x-CH_3 \quad (II)$$

in which x denotes an integer from 2 to 6.

A catalyst system of this type has already been employed in the selective addition of HFPO to perfluorinated carbonyl fluorides. (EP-A-0,070,635, German Offenlegungsschrift No. 3,130,859, EP-A-0,150,618). The advantage of this catalyst system herein lies in the selective addition of HFPO to the carbonyl fluoride employed combined with a simultaneous low yield of undesired oligomerisation products of HFPO. It was therefore surprising that this catalyst system in particular is capable of effecting the specific oligomerisation of HFPO to the trimer or to the tetramer and high conversion rates of HFPO.

In the process according to the invention, the oligomerisation of HFPO is carried out using a catalyst system which comprises a mixture of an alkali metal fluoride, a carboxylic acid dinitrile and a polyethylene glycol dimethyl ether. Potassium fluoride, sodium fluoride and cesium fluoride, in particular potassium fluoride, are primarily suitable as alkali metal fluorides for the catalyst system according to the invention. The dinitriles of saturated aliphatic dicarboxylic acids having 5 to 8 carbon atoms, preferably adiponitrile, are preferably used as carboxylicacid dinitriles. Preferred polyethylene glycol dimethyl ethers are the dimethyl ether of tri-, tetra- or pentaethylene glycol, in particular tetraethylene glycol dimethyl ether.

The three components of the catalyst system are preferably employed in an amount ratio of (2–30) % by weight of alkali metal fluoride: (50–95) % by weight of dinitrile: (2–50) % by weight of polyether, relative to the total catalyst system.

A mixture of trimer and tetramer which still contains proportions of dimer and pentamer is obtained. At the same time, a greater concentration of polyether in the catalyst system leads to an increase in the average degree of oligomerisation and the rate of reaction. In this manner, by reaction in the presence of lower concentrations of polyether, the trimer or, by reaction in the presence of larger concentrations of polyether, the tetramer can be obtained specifically as main components. At the same time, a narrow molecular weight distribution is achieved using this catalyst system. Increasing the relative proportion by weight of alkali metal fluoride in the catalyst mixture at a constant ratio of the two other catalyst components likewise leads to an increase in the average degree of oligomerisation.

The relative composition of the oligomer mixture can furthermore also be controlled by selection of the reaction temperature. Increasing the reaction temperature leads to a lowering of the degree of oligomerisation, a lowering of the reaction temperature causes the reverse.

A further substantial advantage of the process according to the invention in addition to the selectivity is the simple working up of the reaction mixture by phase separation, since the rection product and catalyst mixture are hardly soluble in each other and form a two-phase mixture. In this manner, the catalyst solution can be used again a number of times; the possibility of carrying out the reaction continuously is also given by this. A particular advantage is the use of simple and inexpensive catalyst materials.

The catalyst system can be employed as such or can also be diluted with an inert solvent which has a low solvent power for the two oligomeric carbonyl fluorides, such as, for example, aliphatic or aromatic hydrocarbons.

It is expedient to dry the alkali metal fluoride at a high temperature before use and to pulverize it finely. The carboxylic acid dinitrile and the ether can be employed directly in commercial purity. The influence of any residual moisture of the catalyst system on the average oligomer distribution can be corrected in the desired direction by variation of the reaction temperature or of the composition of the catalyst mixture.

To carry out the process according to the invention, the catalyst mixture is initially introduced into a vessel which can consist, for example, of glass or rust-free stainless steel and which is equipped with an effective stirrer and the HFPO gas is metered in. It is advantageous to stir vigorously during the entire reaction. The reaction of HFPO proceeds exothermically; the reaction temperature can be between -20° C. to 100° C., preferably the reaction is carried out at temperatures between 0° C. and 80° C.

The reaction can be carried out at atmospheric pressure. However, increased pressure is favorable for a rapid conversion; the reaction is in general carried out at most at the intrinsic pressure of HFPO. The pressure in the reaction vessel can be controlled by adjusting the rate of supply of gaseous HFPO.

The mixture of the oligomeric carbonyl fluorides of the formula (I) precipitates as the lower phase and can be drawn off through a bottom value in the reaction vessel.

The catalyst system can therefore be simply removed and used a number of times. At the same time, it does not matter if a residual amount of product remains in the reaction vessel for the next batch in addition to the catalyst mixture.

Since alkali metal fluoride and ether are partially discharged with the product on using the catalyst mixture a number of times, which would lead to a shift in the product composition, it may be necessary to replenish one or both components before a further experiment.

Carrying out the reaction continuously is possible if the lower product phase is continuously expelled from the reaction vessel via a settling zone and HFPO is metered in at the same rate.

Further working up is in general carried out by distillative separation of the oligomeric acid fluorides which can be obtained in purities above 99% by weight in this manner.

EXAMPLE 1

30 g of potassium fluoride, 500 ml of adiponitrile and 100 ml of tetraethylene glycol dimethyl ether were added to a 5 l steel autoclave equipped with a stirrer and the mixture was stirred for 30 min. HFPO under pressure was then added with good stirring, an exothermic reaction setting in. The internal temperature of the reactor was kept at 35°-40° C. by external cooling and the pressure was adjusted to 3.5 bar overpressure in the reaction vessel by regulation of the inflow of gaseous HFPO. In total, 5 kg of HFPO were metered in in the course of 2½ hours. The batch was subsequently stirred until the overpressure decreased (about 3 hours). The reaction mixture rapidly separated into two phases. The lower phase (4.90 kg) containing the reaction product was drawn off through a bottom valve (the upper phase is the catalyst mixture). The reaction product had the following composition (according to gas chromatography of a sample esterified with methanol):

$$CF_3CF_2 \left[ CF_2-O-CF(CF_3) \right]_{n-1} COF$$

| | % by weight | b.p. |
|---|---|---|
| n = 2 | 21.5 | 56–57° C. |
| n = 3 | 61.1 | 114–116° C. |
| n = 4 | 16.3 | 162–163° C. |
| n = 5 | 0.8 | 201–203° C. |

EXAMPLE 2

The oligomerisation was carried out at a reaction temperature of 20°-25° C. under otherwise identical conditions in the same apparatus as in Example 1. 5 kg of HFPO were metered in in the course of 2 hours. The batch was stirred until the overpressure had decreased (about 2 hours). The lower phase (4.93 kg) containing the reaction product was drawn off. The reaction product had the following composition (according to gas chromatography of a sample esterified with methanol):

$$CF_3CF_2 \left[ CF_2-O-CF(CF_3) \right]_{n-1} COF$$

| | % by weight |
|---|---|
| n = 2 | 15.2 |
| n = 3 | 56.8 |
| n = 4 | 25.8 |
| n = 5 | 2.1 |

EXAMPLE 3

A catalyst mixture of 50 g of potassium fluoride, 400 ml of adiponitrile and 200 ml of tetraethylene glycol dimethyl ether was initially introduced into the same apparatus as in Example 1. 5 kg of HFPO were metered in in the course of 2 hours, the internal temperature being kept at 20°-30° C. by cooling of the reaction vessel. The pressure was kept at 1 to 2 bar overpressure. The batch was stirred until the overpressure had decreased (about ½ hour). The product phase (4.94 kg) was separated off. The reaction product had the following composition (according to a sample esterified with methanol):

$$CF_3CF_2 \left[ CF_2-O-CF(CF_3) \right]_{n-1} COF$$

| | % by weight |
|---|---|
| n = 2 | 3.1 |
| n = 3 | 26.2 |
| n = 4 | 47.7 |

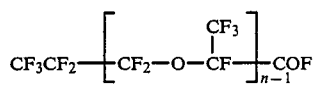

| | % by weight |
|---|---|
| n = 5 | 19.7 |
| n = 6 | 3.1 |

EXAMPLE 4

50 g of potassium fluoride, 300 ml of adiponitrile and 10 ml of tetraethylene glycol dimethyl ether were added to a 2 l autoclave equipped with a stirrer and the mixture was stirred for 30 minutes. HFPO was metered in with good stirring. The internal temperature of the reactor was kept at 35 to 40° C. by external cooling and the pressure in the reaction vessel was adjusted to 3.5 bar overpressure. 1.5 kg of HFPO were metered in in the course of 2 hours.

The batch was stirred for ½ hour, then 1 kg of the lower phase containing the reaction product was drawn off through a bottom valve. 1 kg of HFPO was then again metered into the reaction vessel under the preceding reaction conditions. This process was repeated a number of times, 10 ml of tetraethylene glycol dimethyl ether being added after each second batch. The product phase from the first batch and the product phase after repeating the cycle 14 times had the following composition (in each case in % by weight):

| | 1st batch | 14th batch |
|---|---|---|
| n = 2 | 18.9 | 23.2 |
| n = 3 | 60.6 | 59.2 |
| n = 4 | 19.6 | 16.8 |

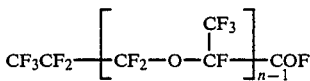

| | 1st batch | 14th batch |
|---|---|---|
| n = 5 | 0.9 | 0.7 |

We claim:

1. A process for the preparation of perfluorinated carbonyl fluorides of the formula

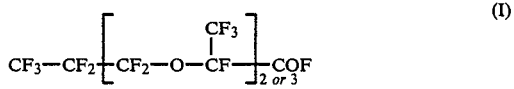

by oligomerisation of hexafluoropropene oxide in the presence of a catalyst, wherein the catalyst comprises an alkali metal fluoride, a carboxylic acid dinitrile and an ether of the formula $$CH_3-O-(CH_2CH_2-O)_x-CH_3 \quad (II)$$

in which x denotes an integer from 2 to 6.

2. The process as claimed in claim 1, wherein potassium fluoride is used as alkali metal fluoride.

3. The process as claimed in claim 1, wherein a dinitrile of a saturated aliphatic dicarboxylic acid having 5 to 8 carbon atoms is used as carboxylic acid dinitrile.

4. The process as claimed in claim 1, wherein adiponitrile is used as carboxylic acid dinitrile.

5. The process as claimed in claim 1, wherein the dimethyl ether of tri-, tetra- or pentaethylene glycol is used as ether of the formula (II).

6. The process as claimed in claim 1, wherein tetraethylene glycol dimethyl ether is used as ether of the formula (II).

7. The process as claimed in claim 1, wherein the components of the catalyst system are used in an amount of 2–30% by weight of alkali metal fluoride, 50–95% by weight of carboxylic acid dinitrile and 2–50% by weight of ether, relative to the total catalyst system.

8. The process as claimed in claim 1, wherein the reaction is carried out at a temperature of −20° C. to +100° C.

* * * * *